(12) United States Patent
Cappelletti

(10) Patent No.: US 11,213,977 B2
(45) Date of Patent: Jan. 4, 2022

(54) MOLD FOR FORMING A JOINT SPACER DEVICE OR A PART THEREOF

(71) Applicant: Cossington Limited, Kingston upon Thames (GB)

(72) Inventor: Ava Cappelletti, Cesena (IT)

( * ) Notice: Subject to any disclaimer, the term of this patent is extended or adjusted under 35 U.S.C. 154(b) by 87 days.

(21) Appl. No.: 16/235,235

(22) Filed: Dec. 28, 2018

(65) Prior Publication Data

US 2019/0134858 A1 May 9, 2019

Related U.S. Application Data

(63) Continuation of application No. 14/534,219, filed on Nov. 6, 2014, now Pat. No. 10,207,429.

(51) Int. Cl.
*B29C 33/44* (2006.01)
*A61F 2/30* (2006.01)
*B29L 31/00* (2006.01)
*A61F 2/38* (2006.01)
*A61F 2/36* (2006.01)

(52) U.S. Cl.
CPC .......... *B29C 33/448* (2013.01); *A61F 2/3094* (2013.01); *A61F 2/36* (2013.01); *A61F 2/389* (2013.01); *A61F 2/3859* (2013.01); *A61F 2002/30471* (2013.01); *A61F 2002/30561* (2013.01); *A61F 2002/30672* (2013.01); *A61F 2002/30957* (2013.01); *A61F 2310/00353* (2013.01); *B29L 2031/757* (2013.01)

(58) Field of Classification Search
CPC .... B29C 33/448; A61F 2/3094; A61F 2/3859; A61F 2/36; A61F 2/389; A61F 2002/30471; A61F 2002/30561; A61F 2002/30672; A61F 2002/30957; A61F 2310/00353; B29L 2031/757
See application file for complete search history.

(56) References Cited

U.S. PATENT DOCUMENTS 3,393,890 A * 7/1968 Lemelson ............... B29C 33/12
249/92
3,834,437 A * 9/1974 Swett ...................... A47J 43/20
249/139
5,876,460 A * 3/1999 Bloebaum .......... A61B 17/1604
623/16.11

(Continued)

FOREIGN PATENT DOCUMENTS

WO WO-2013086177 A1 * 6/2013 ............... A61F 2/36

*Primary Examiner* — Leith S Shafi
(74) *Attorney, Agent, or Firm* — Themis Law

(57) ABSTRACT

A mold for forming a joint spacer device or a part thereof includes a rigid container body having a first perimeter profile delimiting a first molding surface configured to shape a first portion of the joint spacer or part thereof; and a rigid cover provided with a second perimeter profile delimiting a second molding surface configured to shape a second portion of the joint spacer or part thereof. The rigid container body and the rigid cover are removably engageable to each other, at the first and the second perimeter profile, so as to delimit a cavity corresponding to the external configuration of the joint spacer or part thereof. The mold includes a weakening system on the rigid container body and on the rigid cover, making them separable into parts to enable the extraction of the spacer device or part thereof, molded therebetween.

13 Claims, 16 Drawing Sheets

(56) References Cited

U.S. PATENT DOCUMENTS

| | | | |
|---|---|---|---|
| 6,361,731 B1 * | 3/2002 | Smith | A61F 2/30942 264/271.1 |
| 8,414,286 B2 * | 4/2013 | Haney | B29C 45/66 425/577 |
| 2009/0175978 A1 * | 7/2009 | Hawkins | B28B 23/024 425/214 |

* cited by examiner

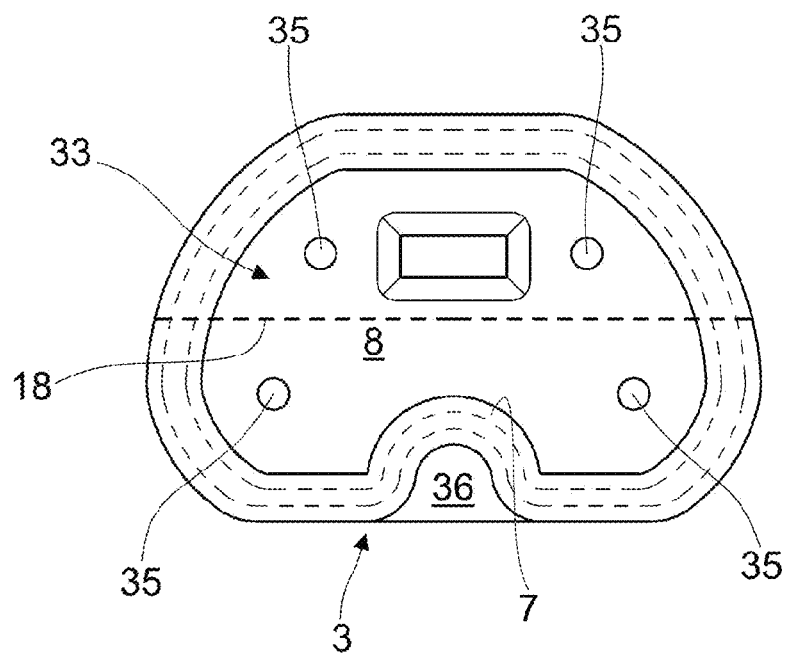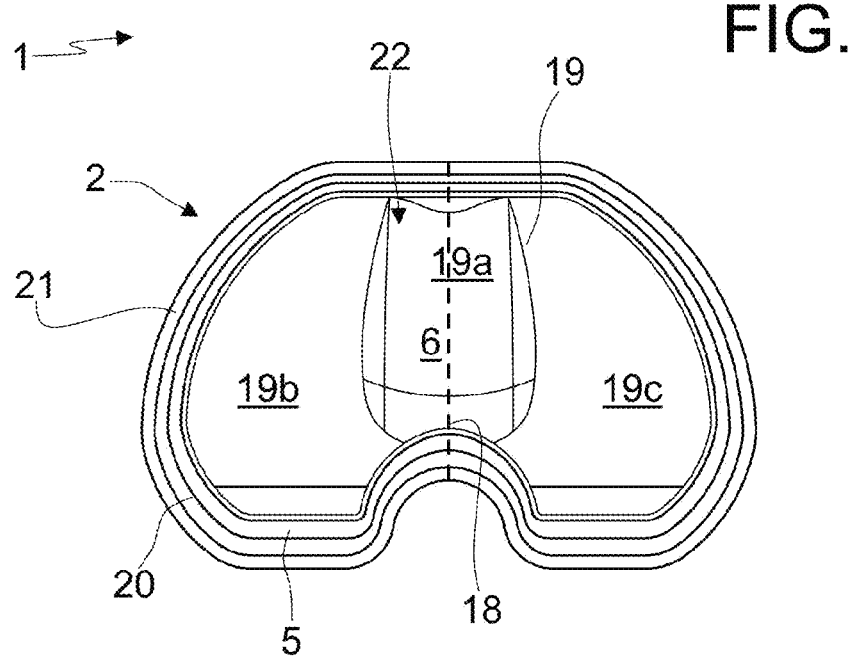
FIG. 6

MOLD FOR FORMING A JOINT SPACER DEVICE OR A PART THEREOF

FIELD OF THE INVENTION

This invention relates to a mold for forming a joint spacer device or a part thereof, and a spacer device obtained with such a mold.

BACKGROUND OF THE INVENTION

Molds for joint spacer devices are known in the art and are usually made of an elastically deformable material, such as, for example, silicone or other elastomeric suitable material. Those molds are adapted to be filled with bone cement supplemented with an antibiotic or other therapeutic substance, when the latter is in the fluid and malleable mass phase, for the purpose of obtaining a finished spacer device.

The bone cement supplemented with the antibiotic or other therapeutic substance, after hardening, is subsequently removed from the mold and the joint spacer thus obtained, after finishing off, is implanted in the joint space of a patient to treat a disease in progress in the tissues surrounding such joint space.

The molds in the prior art suffer from several drawbacks.

In the first place, being these made in elastically yielding-deformable material, such as silicone, they do not allow obtaining a spacer device with a definite shape in optimal manner, for which reason, once extracted from the mold, a spacer device must be machined superficially and finished, in order to obtain the exact required shape.

These molds, furthermore, although being in most cases expected to be disposed of/thrown away after only one single use, at times are reused after an appropriate washing process, for the purpose of reducing the costs for obtaining spacer devices having the same shape.

It can happen, however, that such a washing does not remove completely from the mold the traces of the antibiotic or additive therapeutic substance with bone cement used for a previous spacer device, with the result that allergic reactions may occur in spacer devices made with an antibiotic to which a patient is not allergic, which was, however, made in a mold used previously with bone cement supplemented with an antibiotic to which the patient is allergic.

SUMMARY OF THE INVENTION

Therefore, it is the main object of the present invention to improve the state of the art in the industry sector of molds for the forming of joint spacer devices or a part thereof.

It is another object of the present invention to provide a mold for the forming of a joint spacer device or a part thereof with an alternative configuration with respect to traditional molds.

It is another object of the present invention to provide a mold for the forming of a joint spacer device or a part thereof that cannot be used more than once.

It is a further object of the present invention to provide a mold for the forming of a joint spacer device or a part thereof, which does not require laborious finishing steps of the spacer extracted thereof.

It is still another object of the present invention to provide a mold for the forming of a joint spacer device or a part thereof, which is easy to make at competitive costs.

Not the least object of the present invention is that of providing a joint spacer device or a part thereof obtained by means of such a mold.

According with an aspect of the present invention a mold is provided for forming a joint spacer device or a part thereof according to claim 1.

Dependent claims refer to preferred and advantageous embodiments of the invention.

BRIEF DESCRIPTION OF THE DRAWINGS

Further characteristics and advantages of the present invention will become more evident from the detailed description of some examples of preferred embodiments of a mold for forming a joint spacer device or a part thereof, shown and described by way of example, but not limited thereto, in the attached table of drawings wherein:

FIG. 6 is a plan view of a mold for forming a part of a joint spacer device for the joint of the knee according to a second embodiment of the present invention;

In the attached drawings equal parts or components are marked by the same reference numerals.

DETAILED DESCRIPTION OF EMBODIMENTS OF THE INVENTION

Figure 1:
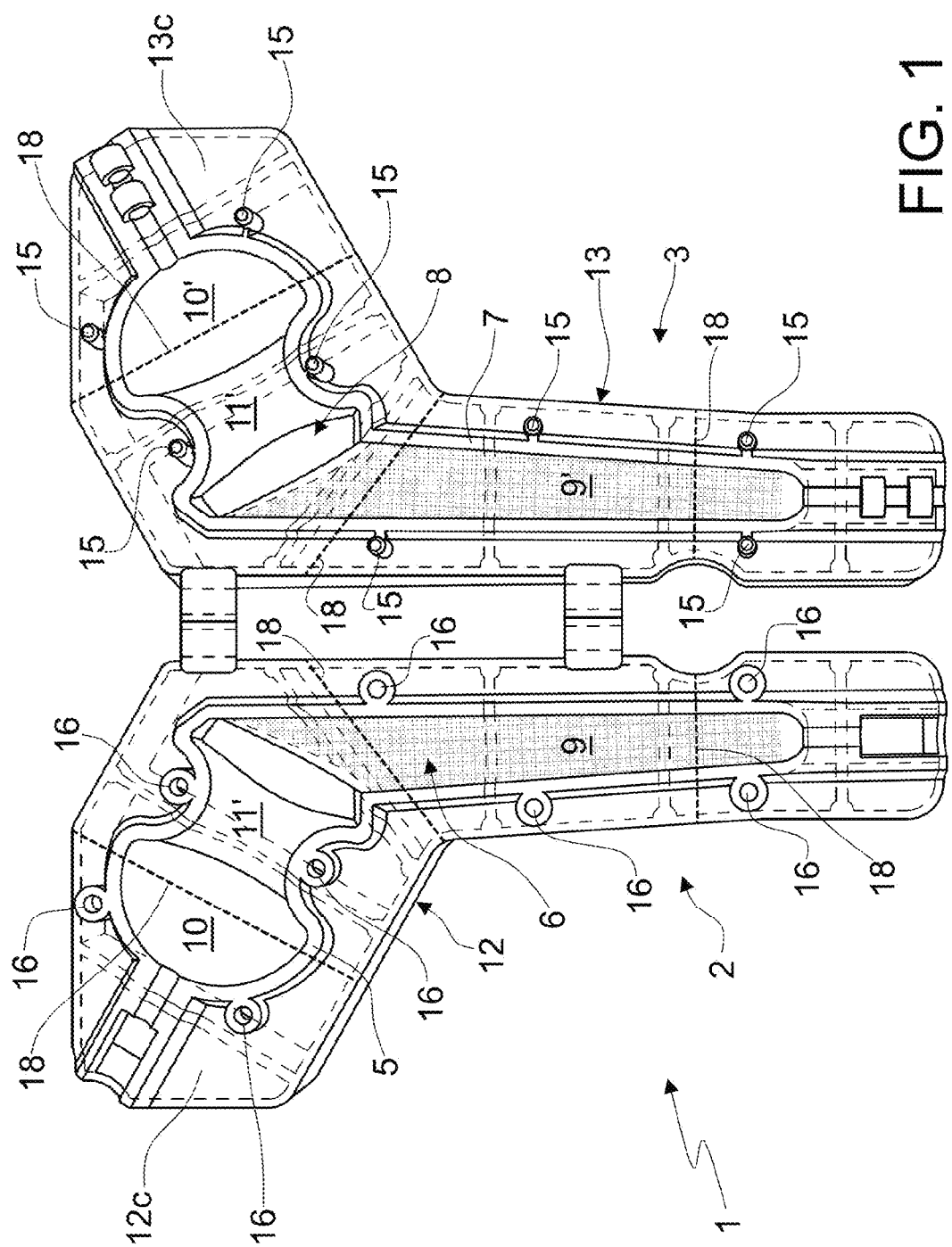
FIG. 1 is a plan view of a mold for forming a joint spacer device for the hip-joint according to a first embodiment of this invention.

With reference to the attached figures, a mold according to this invention is generally indicated with number 1.

Mold 1, according to the present invention, is made in elastically undeformable plastic material, for example polyethylene, and, preferably, distinguishable by a high Shore A, comprised between 90 and 150.

Mold 1, comprises at least a rigid container body 2 and at least a rigid cover 3, which can be coupled with each other to delimit a cavity 4 corresponding to an external configuration of a joint spacer to be formed or a part thereof.

More particularly, the rigid container body 2 is provided with at least a first perimeter profile 5, which internally delimits at least a first molding surface 6 intended to shape at least a first part of the joint spacer device. In different embodiments, the joint spacer device may be a hip spacer device or a tibial knee spacer device.

The rigid cover 3 is also provided with at least a second perimeter profile 7, delimiting at least a second molding surface 8 intended to shape at least a second part of such joint spacer device.

The rigid container body 2 and the rigid cover 3 engage with each other in a removable manner at the respective perimeter profiles 5 and 7, so that the cavity 4 remains circumscribed therebetween.

Figure 2:
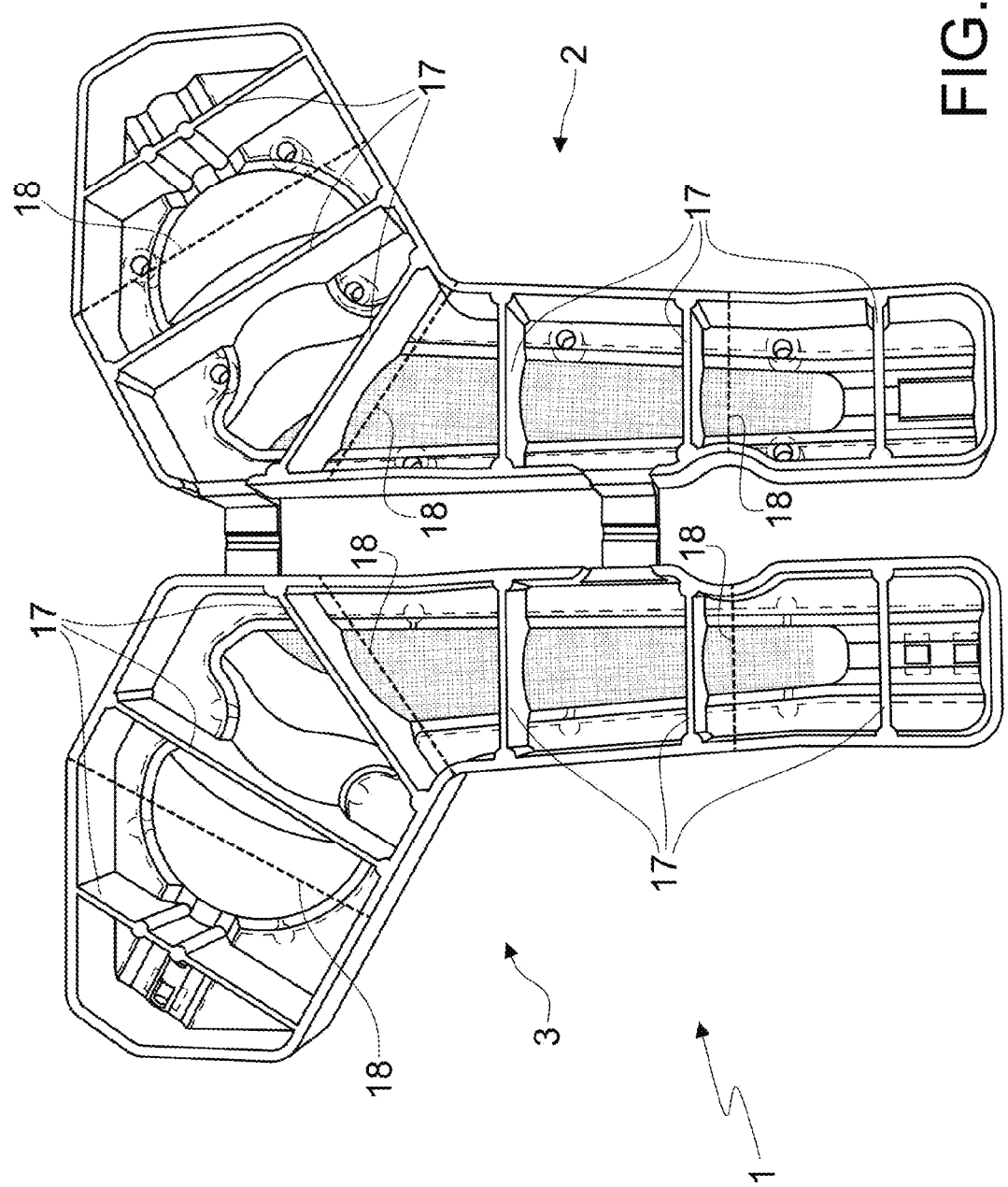
FIG. 2 shows a rear view of the mold of FIG. 1.
Figure 3:
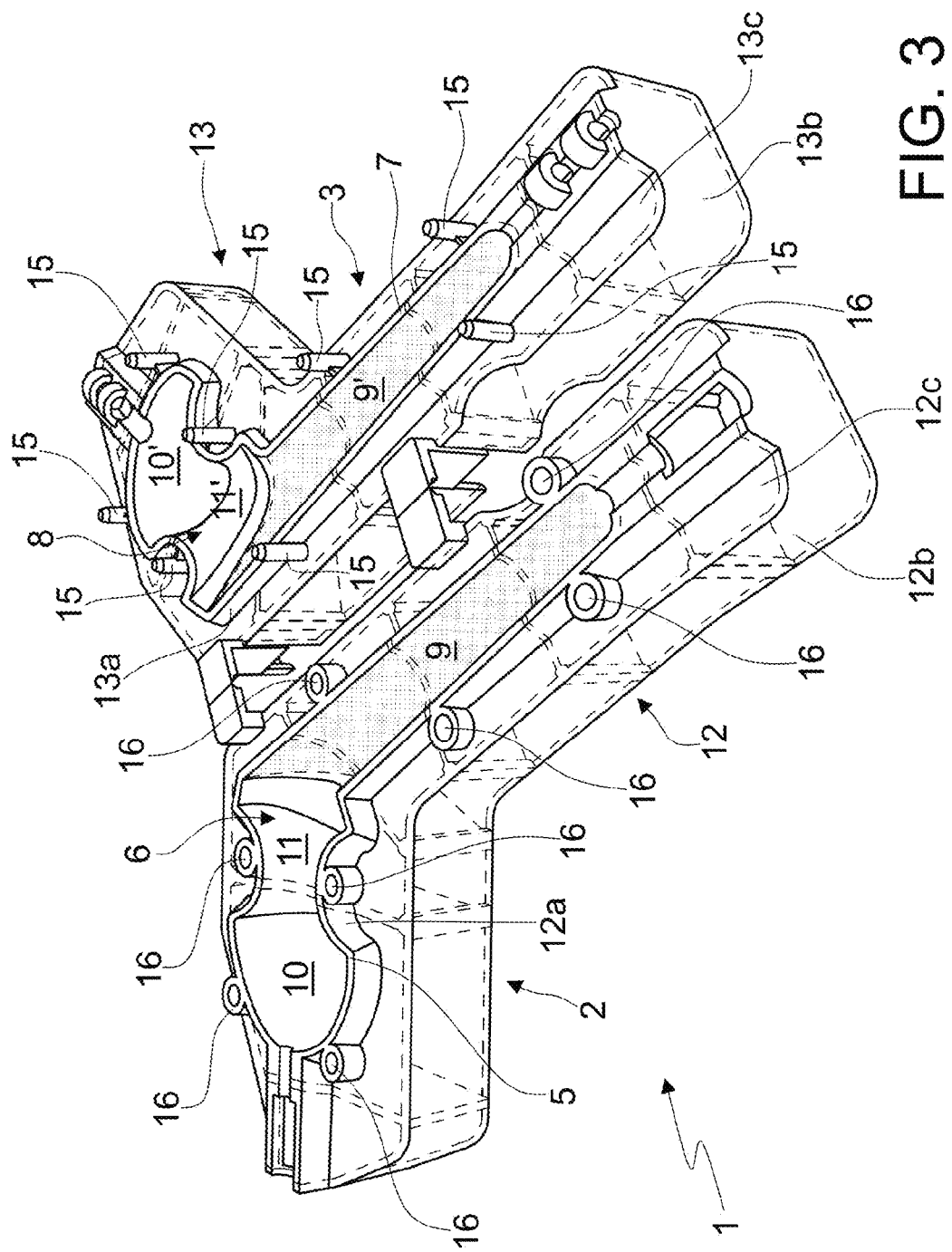
FIG. 3 illustrates a perspective view in side elevation of the mold of FIG. 1.
Figure 4:
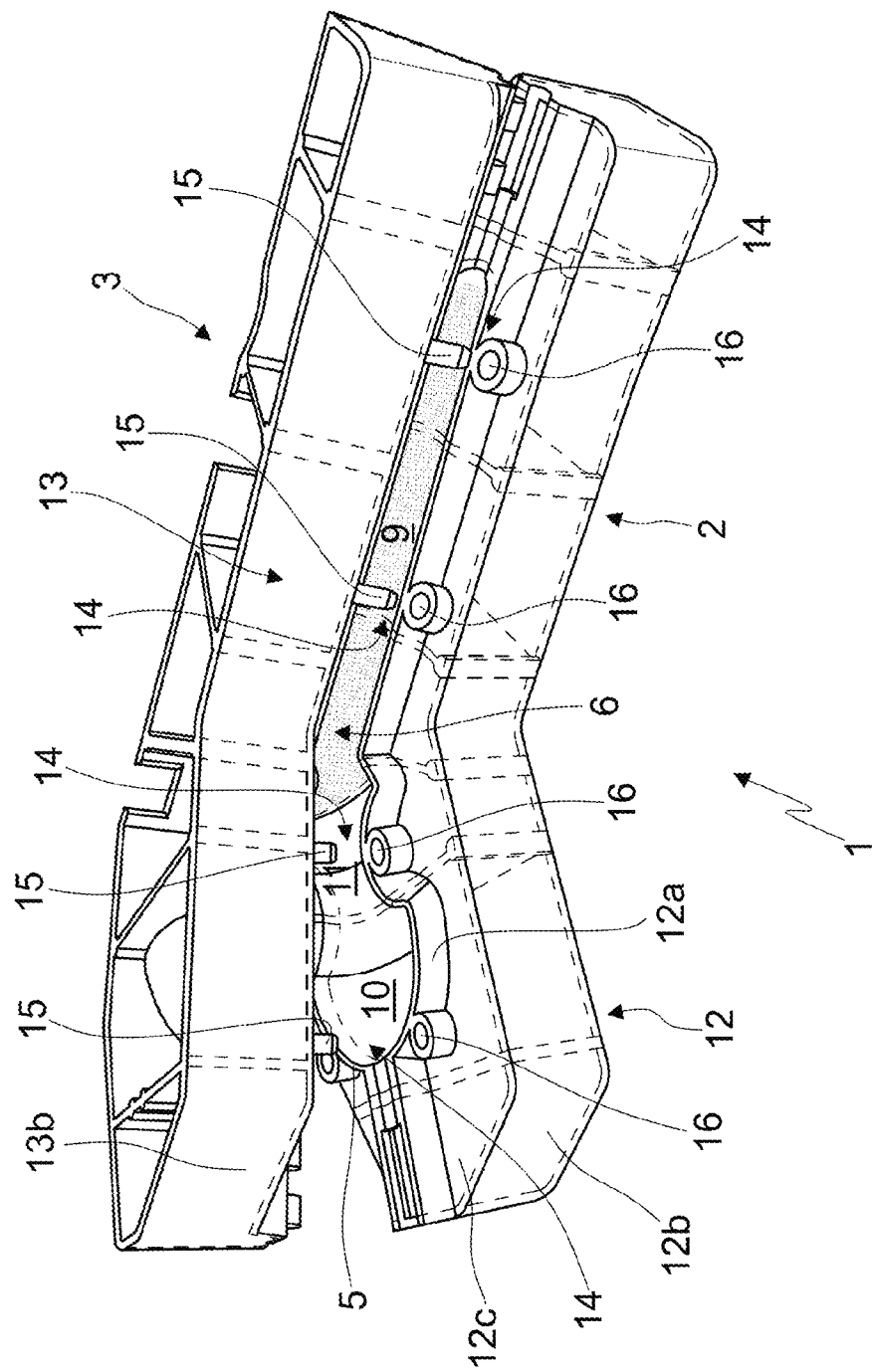
FIG. 4 is a perspective view in side elevation of the mold of FIG. 1 in an intermediate position between an opening position and a closing position.
Figure 5:
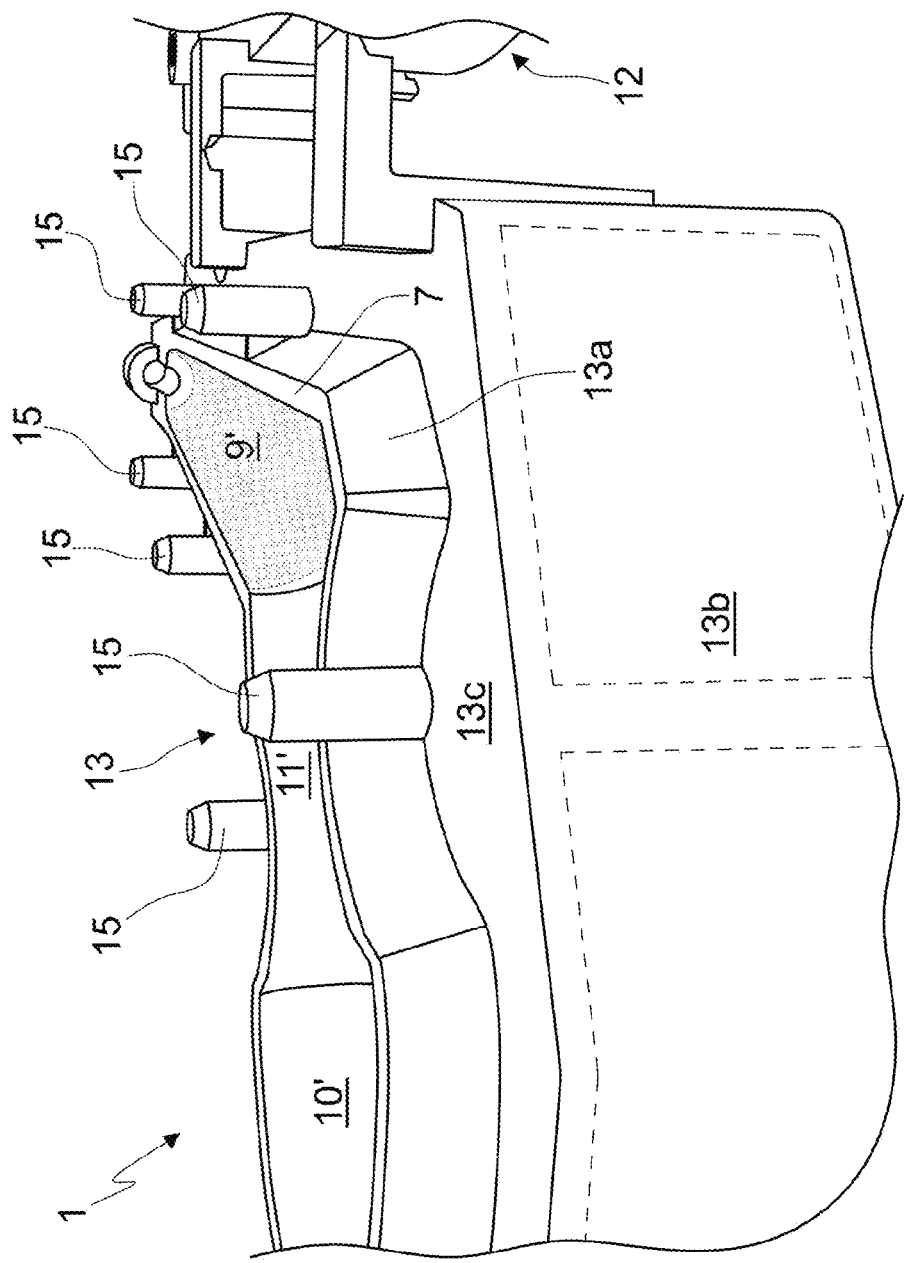
FIG. 5 shows a detail of the mold of FIG. 1.

With particular reference to FIGS. 1 to 5, which illustrate a mold for forming a joint spacer device according to a first embodiment of this invention, it will be noted that, in such a mold, the perimeter profile 5 of the rigid container body 2 circumscribes a forming surface for a longitudinal half of a joint spacer device for hip, and the perimeter profile 7 of the rigid cover 3 circumscribes a second molding surface 8 for the other longitudinal half of such a spacer device.

Each molding surface 6 and 8 comprises a stem portion 9, 9', a head portion 10, 10', and a connection portion 11, 11' between the stem portion and the head portion.

In the mold according to the first embodiment of the present invention the perimeter profiles 5 and 7 coincide with the access opening to the container body 2 and the cover 3, respectively. across the access opening it is possible to cast the bone cement supplemented with a suitable antibiotic, pouring it on the first molding surface 6 and on the second molding surface 8, so as to cover them up to the level of the respective perimeter profile 5, 7.

According to a variation of the mold according to the invention, the molding surfaces 6 and 8 are each obtained in a respective support base 12, 13, and each perimeter profile 5 and 7 extends substantially orthogonally from the respective base and away from it.

Between the upper end of each perimeter profile 5, 7 and the support base 12, 13 the mold according to the present invention comprises at least an inclined plane perimeter wall 12a, 13a. The inclined plane perimeter walls 12a, 13a of the rigid container body 2 and of the rigid cover 3, besides carrying out a stiffening function of the respective perimeter profile 5, 7, facilitate, in addition, the disposal of the bone cement poured in excess on the molding surfaces 6 and/or 8 during the forming stage.

The mold according to the invention, as already mentioned above, is configured in such a manner that, once the bone cement is poured on the molding surfaces 6, 8 and after a certain time has passed for the partial hardening thereof, the rigid container body 2 and rigid cover 3 are engaged with each other and delimit a cavity 4 of finite size. The bone cement therefore, which can be accidentally poured in excess on the molding surfaces 6 and/or 8, outflows sideways at the perimeter sections and it separates distinctly from the bone cement contained in the cavity 4, thanks to the inclined plane perimeter walls 12a and 13a that facilitate its removal. It follows that, once the bone cement has completely hardened and it has been separated from the mold, as it will be better said hereinafter, the hip spacer device thus obtained comprises a minimum perimeter edge (of width equal to the maximum of that of the perimeter profiles 5 and 7) and requires, therefore, minimum finishing work before the implantation in situ.

For the removable type engagement between the rigid container body 2 and the rigid cover 3, the mold according to the first embodiment of this invention comprises removable engagement means 14 of the male 15 and female 16 types.

Such removable engagement means 14 are provided in positions at, and along, each perimeter profile 5, 7, so that, when the rigid container body 2 and the respective rigid cover 3 engage with each other at their respective perimeter profiles 5 and 7, the engagement between the male engagement means 15 and the female engagement means 16 of the mold (see, in particular, FIG. 4) is also achieved.

According to a variation illustrated in the figures of the first embodiment of this invention, the rigid container body 2 and the rigid cover 3 are hinged with each other at the respective bases 12, 13.

Each base 12, 13 can, furthermore, comprise a solid body made of suitable plastic material as described above, wherein the respective molding surface 6, 8 is hollowed out. Alternatively, it can comprise side walls 12b, 13b, delimiting at the top a base surface 12c, 13c from which the respective perimeter profile 5, 7 of the rigid container body 2 and the rigid cover 3 rise. In this case, each base 12 and/or 13 can comprise, between the side walls, lower with respect to the rigid container body 2 and/or the cover 3, one or more transversal stiffening ribs 17, so that the mold 1 according to the invention is elastically undeformable although being made with a reduced quantity of material.

Now, the mold 1 according to the first embodiment of the present invention comprises weakening means 18 on the rigid container body 2 and on the rigid covers 3, so that both the container body and the cover can be separated in several parts in order to allow extraction of the spacer device that has been formed.

Such weakening means, illustrated schematically in the drawings, comprise at least a reduced thickness line (indicated merely by way of example in FIGS. 1 and 2 with dashed lines), at which the rigid container body 2 and the rigid cover 3 can be separated in several parts. Such a reduced thickness line is provided transversally and/or longitudinally on both the rigid container body 2 and the rigid cover 3.

Figure 7:
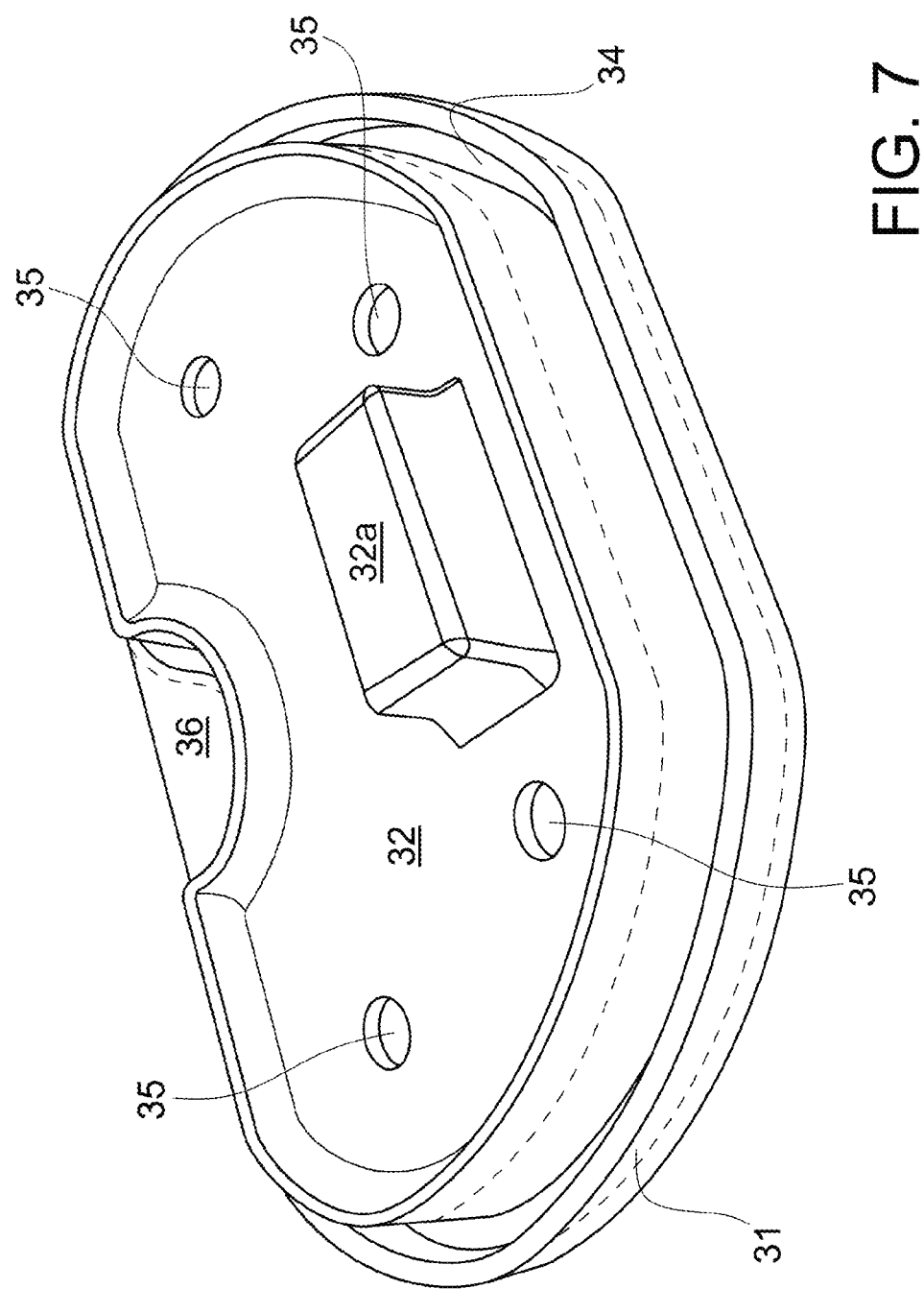
FIG. 7 shows a perspective view of the mold cover of FIG. 6.
Figure 8:
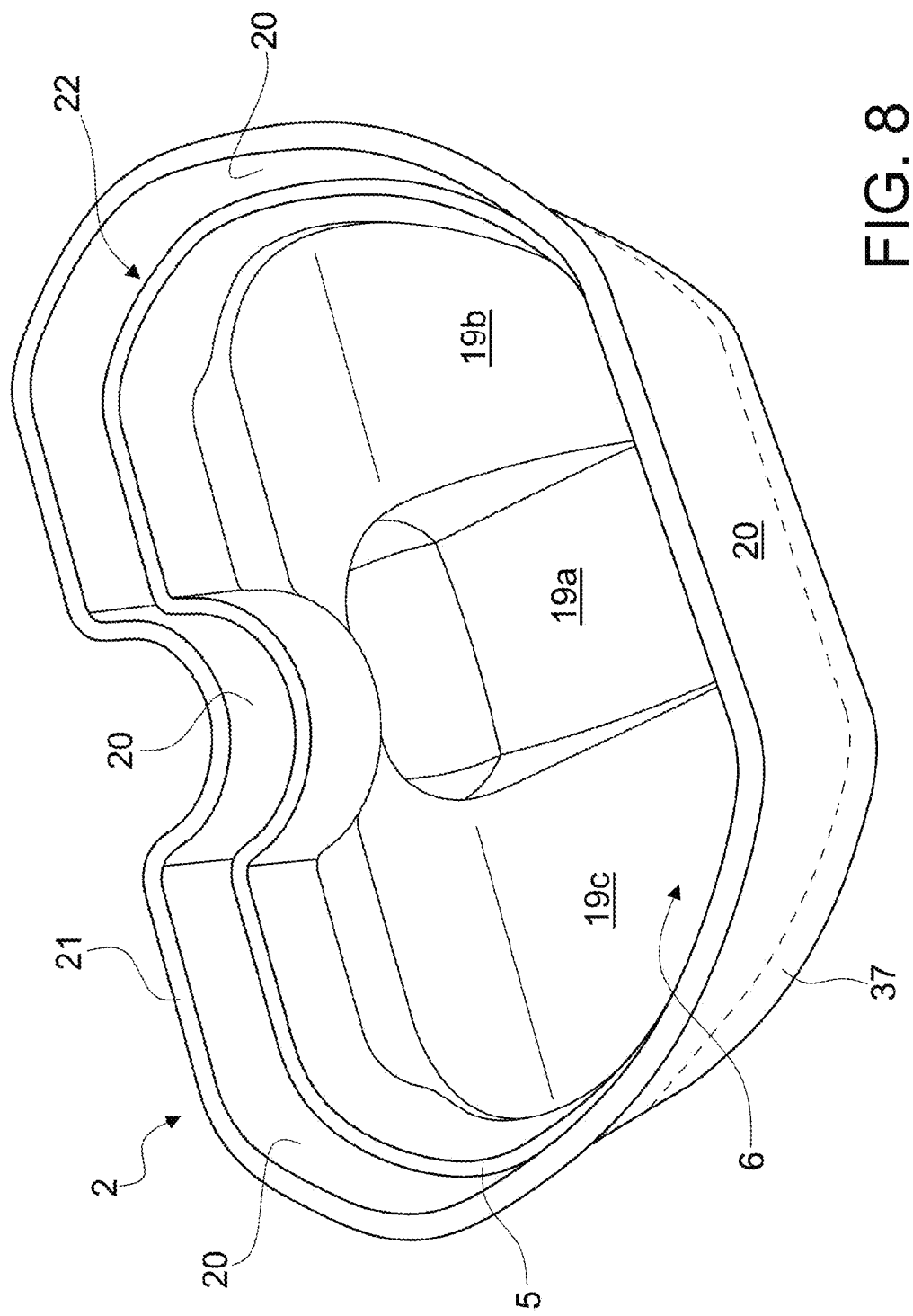
FIG. 8 illustrates a perspective view of the mold container body of FIG. 6.
Figure 9:
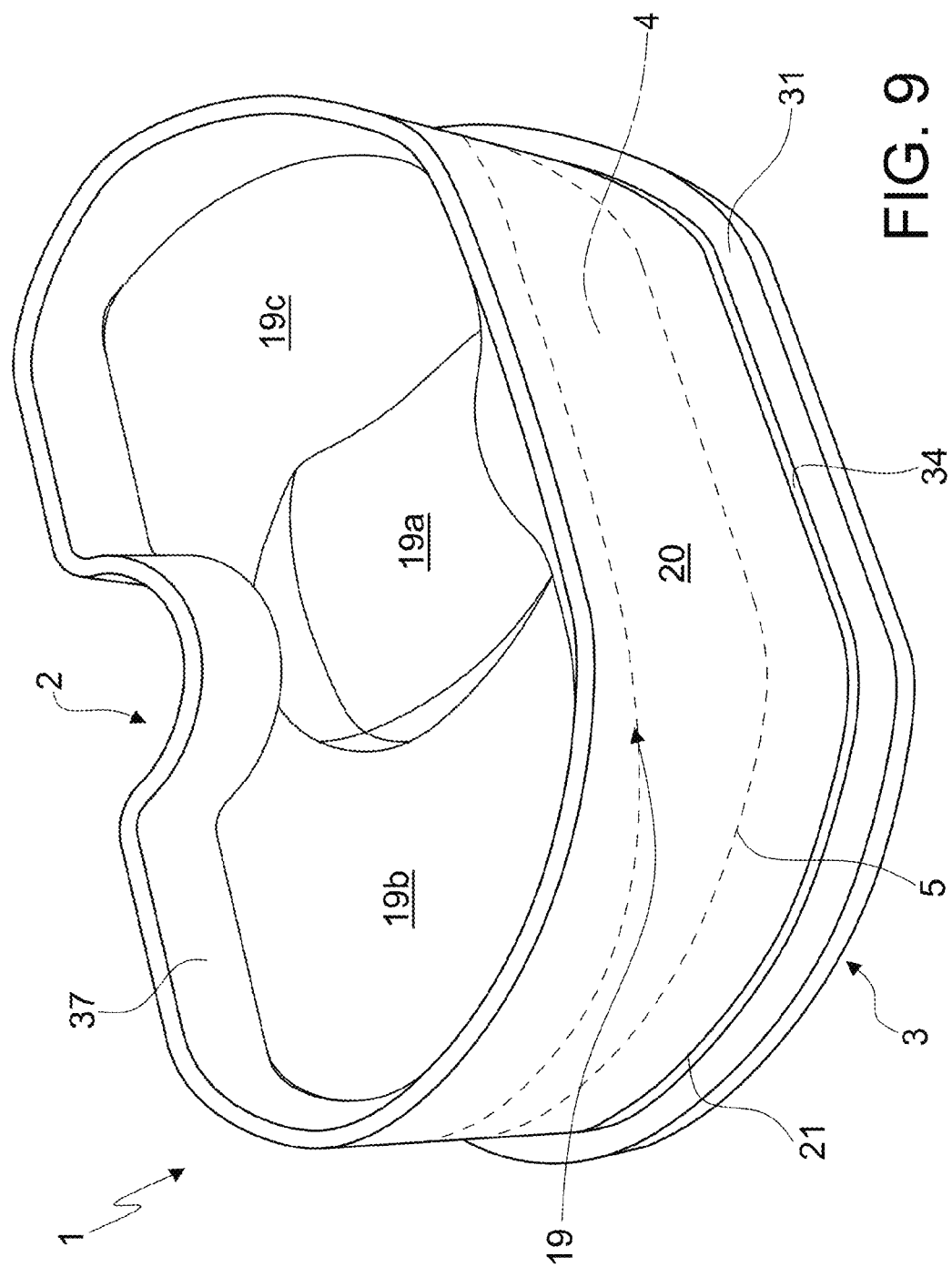
FIG. 9 is a perspective view of the mold of FIG. 6 with container body and cover engaged with each other thereby delimiting a forming seat.
Figure 10:
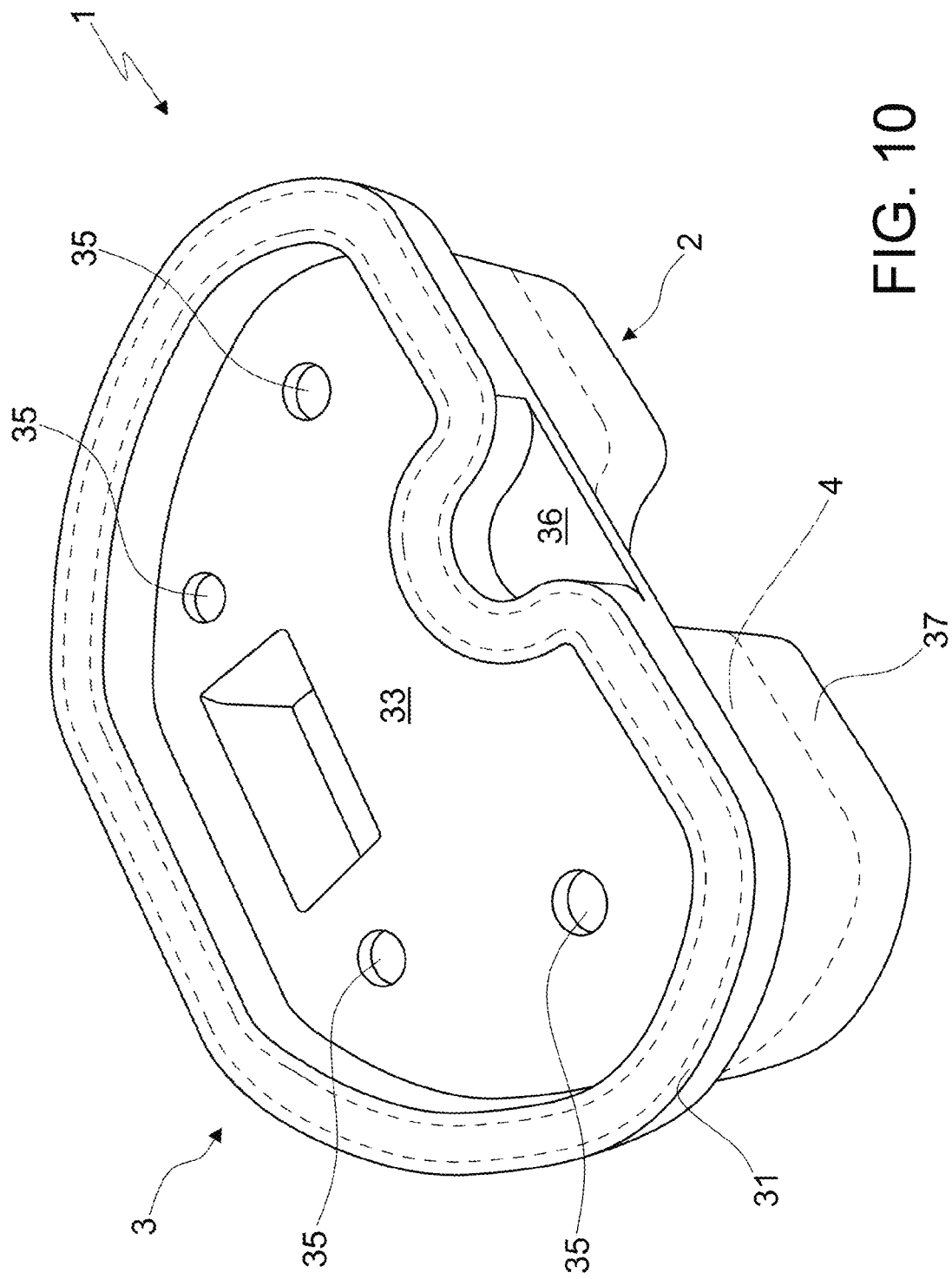
FIG. 10 shows another perspective view of the mold of FIG. 6, wherein container body and cover are engaged with each other.

The mold 1 according to a second embodiment of the present invention, see in particular the annexed FIGS. 6 to 10, is particularly suitable for forming a tibial portion of a spacer device for knee joint and comprises at least a rigid container body 2 and at least a rigid cover 3, which can be coupled with each other to delimit a cavity 4 corresponding to the external configuration of such component or tibial part.

More particularly, the rigid container body 2 of the mold according to the invention has a substantially "C"-shaped plan configuration and comprises a bottom wall 19 from which side walls 20 rise. The side walls 20 end at the top with an edge 21, at an upper access opening 22.

The rigid container body 2 is provided with at least a first perimeter profile 5, which upperly delimits at least a first molding surface 6 intended to shape at least a first part of the joint spacer device.

The first perimeter profile 5 is defined by an internal shoulder at the side walls 20, at a distance substantially constant from the edge 21.

Also the rigid cover 3 has a substantially "C"-shaped plan configuration and is provided with at least a second perimeter profile 7, delimiting at least a second molding surface 8, intended to shape at least a second part of such joint spacer device.

The rigid container body 2 and the rigid cover 3 are engageable with each other in a removable manner at their respective perimeter profiles 5 and 7, so that the cavity 4 remains delimited therebetween.

As it will be noted, the bottom wall 19 of the rigid container body 2 of the mold 1 according to the second embodiment of the present invention is substantially convex and has a central portion 19a and two end portions 19b and 19c, at the free ends of the "C". The central portion 19a is substantially in bas-relief with respect to the end portions 19b and 19c.

Now, with reference to the rigid cover 3 of the mold of FIGS. 6 to 10, it will be noted how this has a lower surface 32, facing, in use, the respective rigid container body 2 and an outer surface 33, facing, in use, externally. The rigid cover 3 comprises furthermore a perimeter edge 31 for the engagement with the edge 21 of the container body 2. To this regard, it will be noted that the cover has, at its lower surface 32, a perimeter recess 34, within which the edge 21 of the rigid container body 2 can be fit inserted, with interference. The edge 31 of the rigid cover 3 encloses externally the edge 21 of the container body 2.

The second perimeter profile 7 of the mold according to the invention is provided on the lower surface 32 of the rigid cover 3, which lower surface 32 is partially insertable in the container body itself, with such perimeter profile 7 in abutment against the perimeter profile 5 and, accordingly, with the internal shoulder of the container 2.

The rigid cover 3 of the mold according to the invention comprises also at least a through opening 35 for the overflow of the bone cement possibly poured in excess in the rigid container body 2. Such a through opening 35 also facilitates the overflow of air bubbles from inside the cavity 4.

The lower surface 32 of the rigid cover 3 comprises a central portion 32a, of substantially rectangular transversal section, extending away from such lower surface 32, and facing, in use, the container body 2.

Now, also the mold 1 according to the second embodiment of the present invention comprises weakening means 18 both on the rigid container body 2 and the rigid cover 3 (indicated in FIG. 6 merely as a way of example with dashed lines), so that they can both be separated in several parts in order to allow extraction of the spacer device formed therein.

Such weakening means, illustrated schematically in the drawing, comprise at least a reduced thickness line, at which the rigid container body 2 and the rigid cover 3 can be separated in several parts. Such a reduced thickness line is provided with transversally and/or longitudinally both on the rigid container body 2 and on the rigid cover 3.

Figure 11:
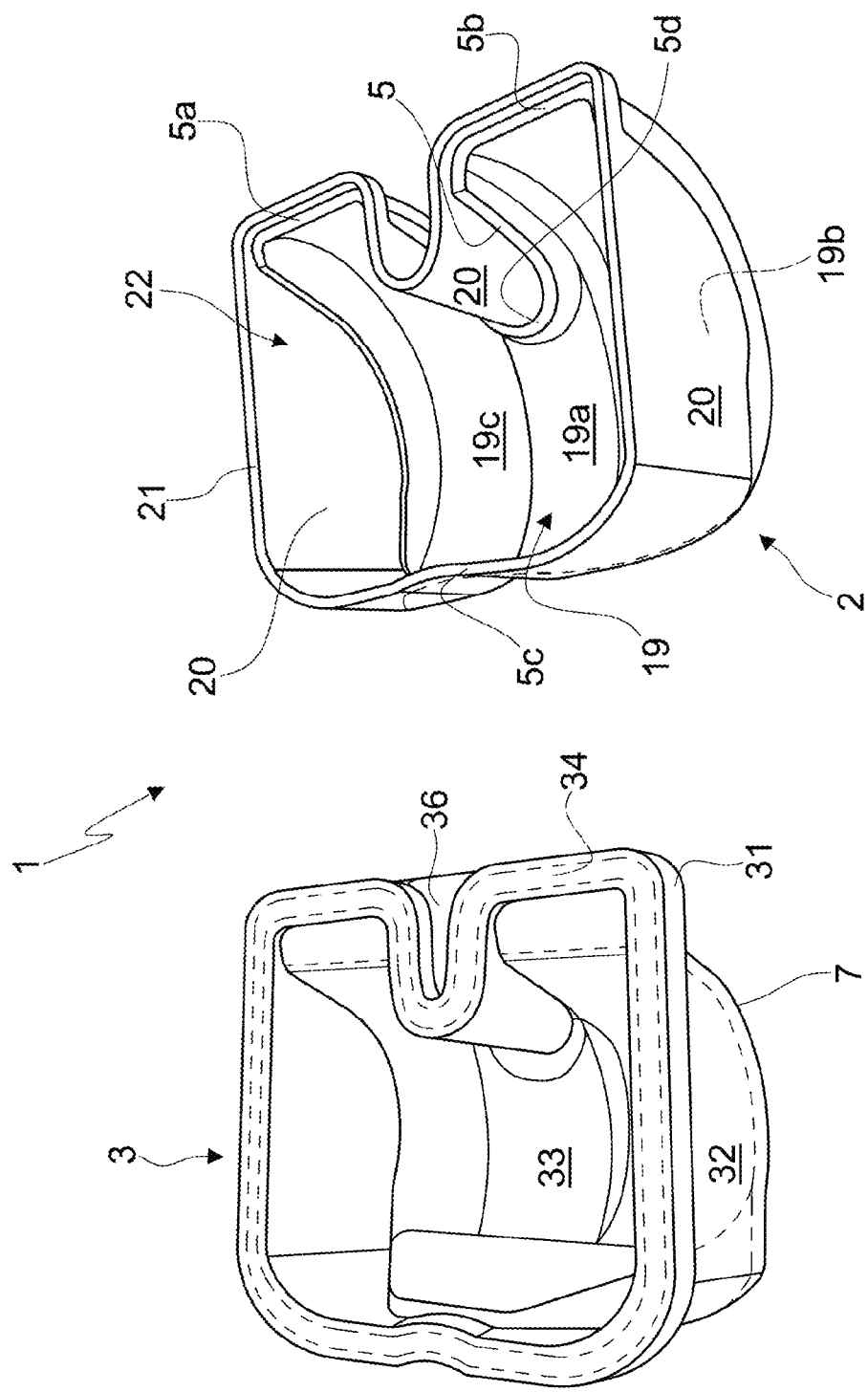
FIG. 11 illustrates a perspective view in side elevation of a mold for forming a part of a joint spacer device according to a third embodiment of this invention.
Figure 12:
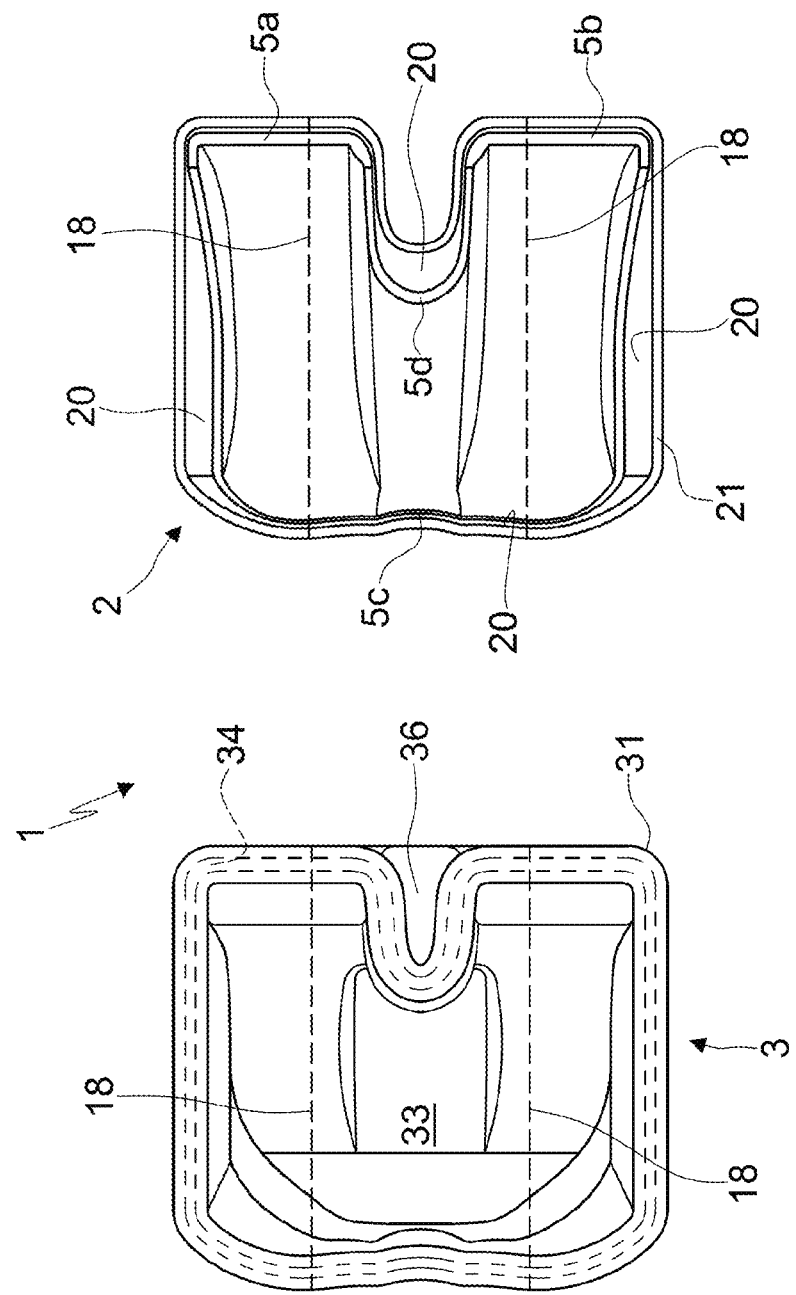
FIG. 12 shows a plan view of the mold of FIG. 11.
Figure 13:
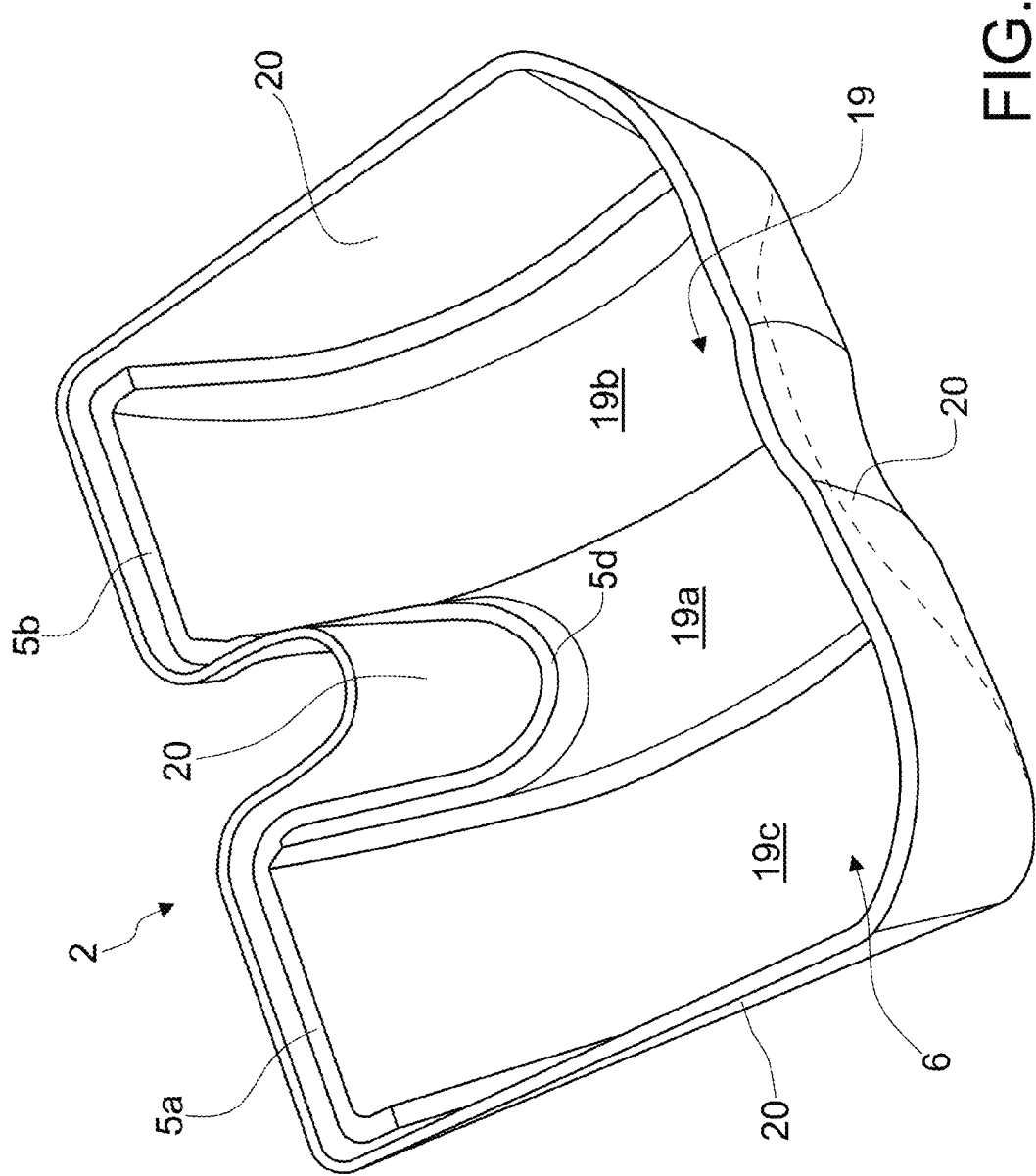
FIG. 13 illustrates a perspective view of the container body of the mold of FIG. 11.
Figure 14:
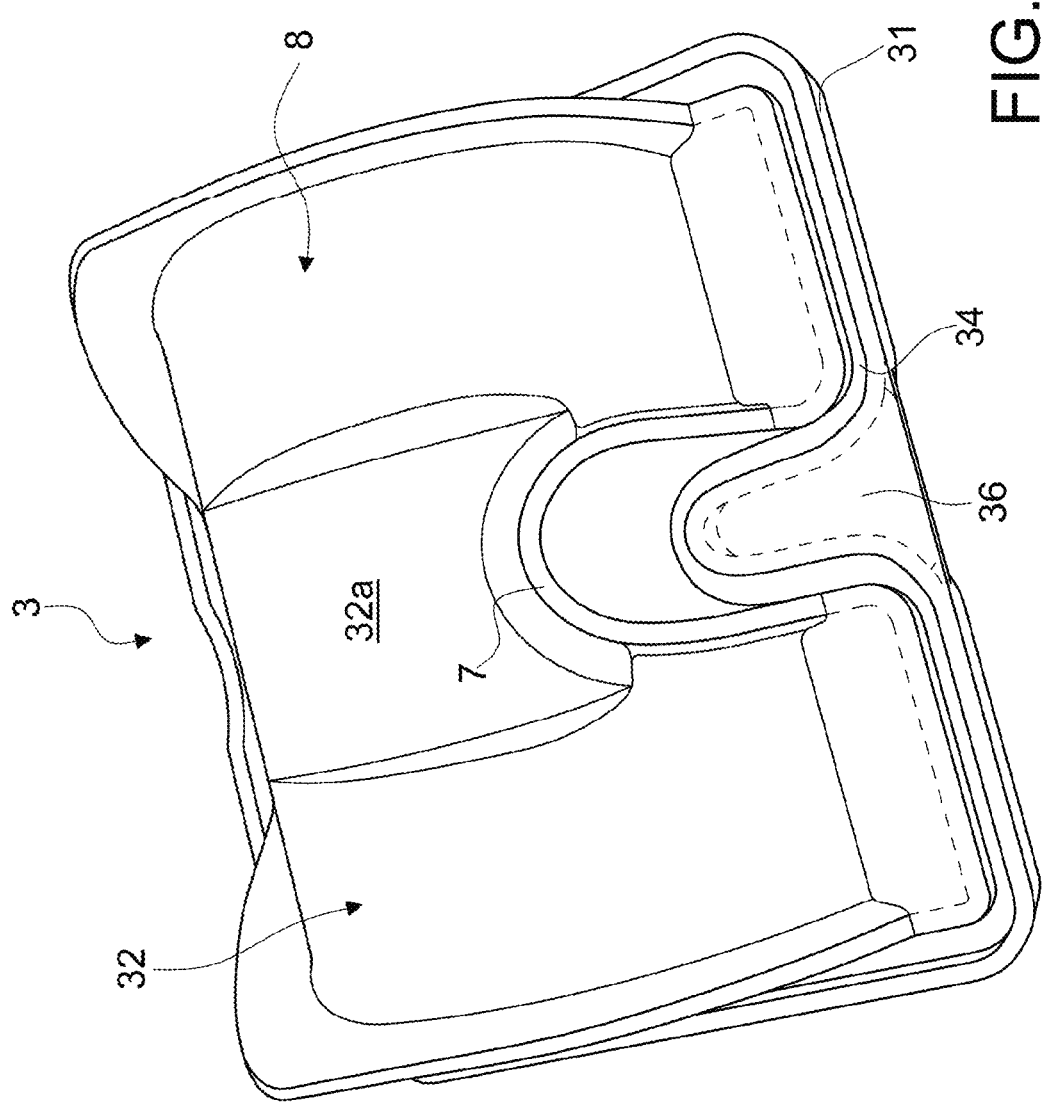
FIG. 14 is a perspective view of the cover of the mold of FIG. 11.
Figure 15:
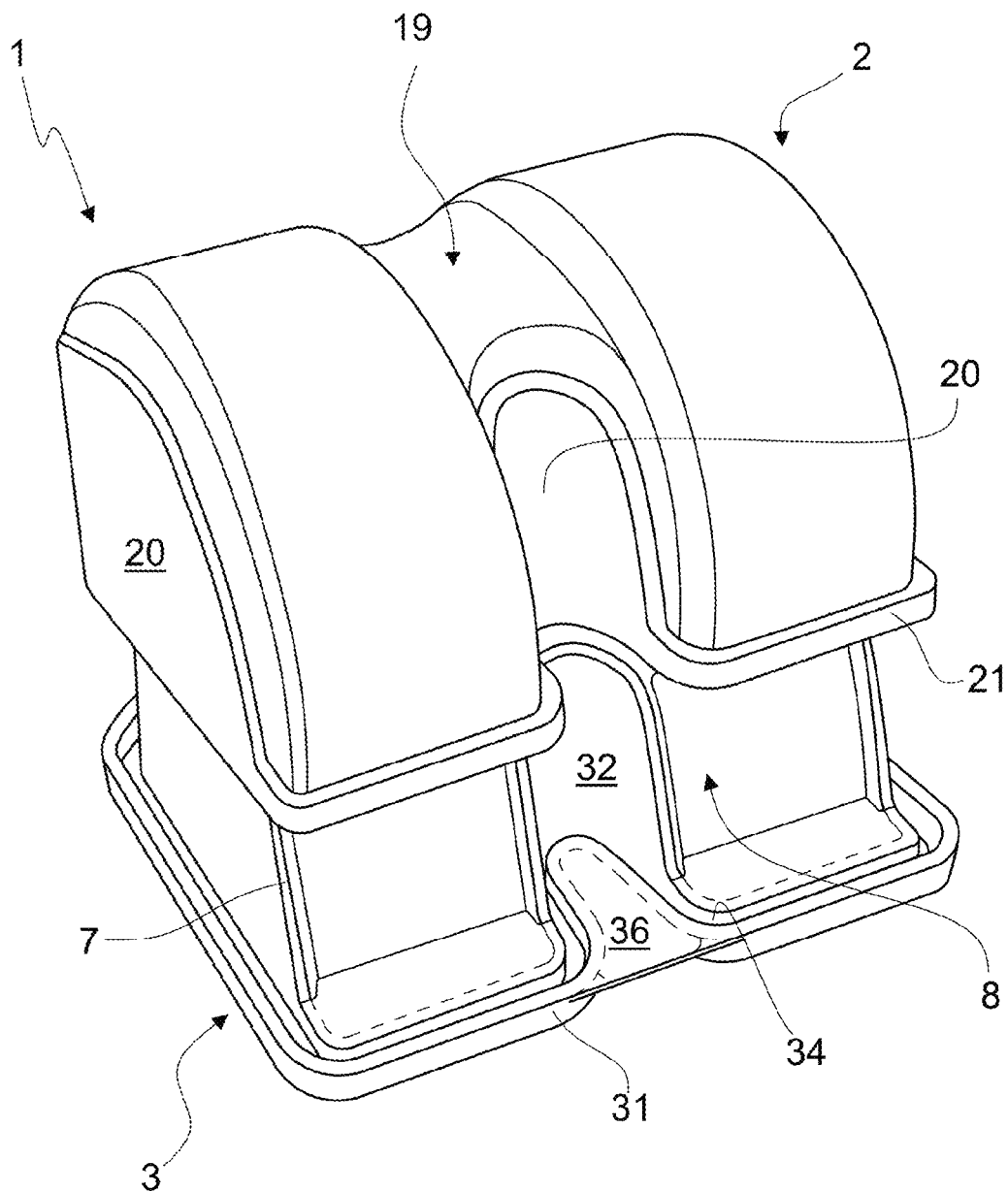
FIG. 15 shows a perspective view in front elevation of the mold of FIG. 11, wherein the container body and the cover are in intermediate position with the cover partly inserted in the container.
Figure 16:
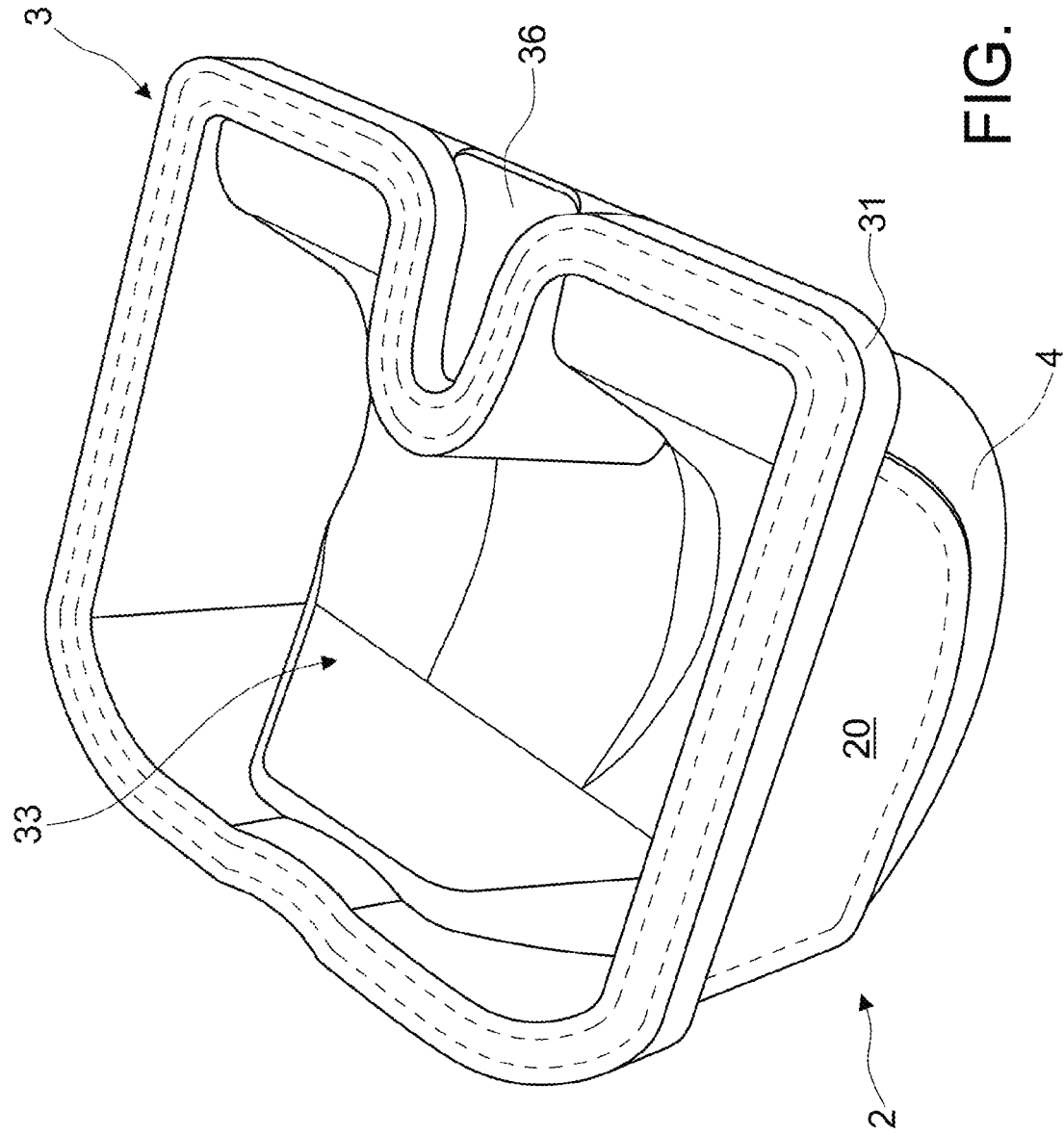
FIG. 16 illustrates a perspective view of the mold of FIG. 11, wherein the cover closes the container body and delimits with the latter the forming seat.

The annexed FIGS. 11 to 16 show the mold for the forming of a joint spacer according to the third embodiment of the present invention, in particular suitable for forming a component or femoral part of a knee joint spacer device. Such a mold comprises at least a rigid container body 2 and at least a rigid cover 3, which can be coupled with each other to delimit a cavity 4 (FIG. 16) corresponding to the external configuration of such component or femoral part.

More particularly, the rigid container body 2 of the mold according to the invention has a substantially "C"-shaped plan configuration and circumscribes a bottom wall 19 from which side walls 20 rise. The side walls 20 end at the top with an edge 21 at an upper access opening 22.

The bottom wall 19 of the container body 2 of the mold 1 according to the third embodiment of this invention is substantially concave and has a central portion 19a and two end portions 19b and 19c, at the free ends of "C". The central portion 19a is substantially in relief with respect to the end portions 19b and 19c.

The rigid container body 2 is provided with at least a first perimeter profile 5, which upperly delimits at least a first molding surface 6 intended to shape at least a first part of the joint spacer device.

The first perimeter profile 5 is defined by an internal shoulder, at the side walls 20 of the rigid container body 2, at a not constant distance from the edge 21 and, therefore, from the bottom wall 19.

More particularly, the perimeter profile 5 of the container body 2 is close to the edge 21 of the container itself at the free ends of the "C" (abutment portions indicated in the figures with the references 5a and 5b) and at an opposite portion, intermediate with respect to such ends (indicated in the figures as 5c). The perimeter profile 5 descends towards the bottom wall 19 of the container body at the remaining end portions 19b and 19c, and at the portion of the side wall 20 comprised between the free ends of "C" (stretch 5d). The remaining portions of the perimeter profile 5 are continuous connection parts, since the perimeter profile 5 is continuous along the side wall 20 of the container 2.

The rigid cover 3 has a substantially "C"-shaped plan configuration and is provided with at least a second perimeter profile 7, delimiting at least a second molding surface 8, intended to shape at least a second part of such joint spacer device.

The rigid container body 2 and the rigid cover 3 are engageable in a removable manner with each other at respective perimeter profiles 5 and 7, so that the cavity 4 remains delimited therebetween.

Now, with reference to the rigid cover 3 of the mold of FIGS. 11 to 16, it will be noted how this has a lower surface 32, facing, in use, the respective rigid container body 2 and an outer surface 33, facing, in use, externally. The rigid cover 3 comprises also a perimeter edge 31 for the engagement with the edge 21 of the container body 2. To this regard it will be noted that the rigid cover 3 has, at its lower surface 32, a perimeter recess 34, within which the edge 21 of the rigid container body 2 can be fit inserted, with interference. The edge 31 of the rigid cover 3 encloses externally the edge 21 of the container body 2.

The second perimeter profile 7 of the mold according to the invention is provided with on the lower surface 32 of the rigid cover 3, which can be inserted in the container body itself with the perimeter section 7 in abutment against the perimeter profile 5, i.e. with the internal shoulder of the rigid container 2. The second perimeter profile 7 of the cover is therefore configured in a corresponding manner to the respective perimeter profile 5.

The cover 3 of the mold according to the invention comprises also at least a through opening (not illustrated in this case in the drawings) for the overflow of the bone cement cast possibly in excess in the rigid container body 2. Such a through opening serves, as previously mentioned with reference to the second embodiment of the present invention, to facilitate the overflow of air bubbles from inside the cavity 4.

The lower surface 32 of the rigid cover 3 is substantially convex (see in particular FIG. 14) and comprises a central portion 32a, recessed with respect to the portions at the free ends of "C". Such recessed portion 32a is intended, in use, to be placed on top of the central portion in relief 19a of the container body.

Now, also the mold 1 according to the third embodiment of this invention comprises weakening means 18 both on the container body 2 and the cover 3, so that both can be separated in several parts to allow extraction of the spacer device formed therebetween.

Such weakening means, illustrated schematically in the drawings by a dashed line (for example in FIG. 12) comprise at least a reduced thickness line, at which the rigid container body 2 and the rigid cover 3 can be separated in several parts. Such a reduced thickness line is provided with transversally and/or longitudinally, both on the rigid container body 2 and the rigid cover 3.

As for the other embodiments described above, the weakening means 18 are provided with in such a position for which it is possible to extract the joint spacer device or a part thereof from the mold without destroying the mold itself.

Now, with reference to the second and the third embodiment of the present invention, it will be noted that the rigid cover 3 can comprise at least a gripping portion 36, between the free ends of the said "C". Such gripping portion facilitates the application of the rigid cover 3 on the rigid container body 2, as well as their separation in several parts thereof.

Both the rigid container body 2 and the rigid cover 3 can, furthermore, comprise at least a stiffening perimeter rib 37, so that they are elastically undeformable. Such rib is optional and, alternatively thereto, it can be envisaged to make the bottom of the container body 2 or the cover with a greater quantity of material in order to provide greater stiffness to the mold.

Furthermore, once the rigid cover 3 is led to close the rigid container body 2, the mold can be kept closed by additional removable engagement means, not illustrated in the drawings, which comprise, for example, clamp engagement means, or clips or hooks, between the container body 2 and the cover 3.

Once closed, with or without the aid of additional engagement means, the mold can be laid on any of its surfaces, without the need to make it maintain a precise position during hardening of the bone cement kept therein.

The molds 1 described above are susceptible to several modifications and variations within the protective scope of the claims that follow.

Thus, for example, if a joint spacer device were to be made for a hip by means of the mold according to the first embodiment of this invention, which joint device were equipped of a metal core or any other suitable material able to provide a greater resistance to forces of the spacer device, such mold would comprise also one or more spacer elements (not illustrated in the figures), for example sleeves fitted on such core or element, in any case capable of supporting it, which could be positioned in a predefined position on one or the other molding surface 6 or 8 and would allow keeping the core of the spacer suitably arranged in the mold, during the forming phase of the joint spacer device.

The invention claimed is:

1. A mold for forming a tibial knee spacer device or part thereof, comprising:
    a rigid container body provided with a first perimeter profile delimiting a first molding surface configured to shape a first portion of the tibial knee spacer device or the part thereof; and
    a rigid cover provided with a second perimeter profile delimiting a second molding surface configured to shape a second portion of the tibial knee spacer device or the part thereof,
    wherein the rigid container body and the rigid cover are removably engageable with each other, at the first and the second perimeter profile, so as to delimit a cavity corresponding to an external configuration of the tibial knee spacer device or the part thereof,
    wherein the mold further comprises weakening means on the rigid container body and on the rigid cover so that both the rigid container body and the rigid cover are separable into parts to enable extraction of the tibial knee spacer device or the part thereof, molded therebetween, and
    wherein the rigid cover comprises a central portion having an essentially rectangular cross section, the central portion protruding from a lower surface of the rigid cover to define a single peak extending from a remainder of the lower surface and facing the rigid container body when the rigid cover engages the rigid container body.

2. The mold according to claim 1, wherein the weakening means on the rigid container body and on the rigid cover comprise a line of reduced thickness, so that the mold is separable into multiple portions at the line of reduced thickness.

3. The mold according to claim 2, wherein the line with reduced thickness is provided transversally and/or longitudinally on the rigid container body and on the rigid cover.

4. The mold according to claim 1, wherein the rigid container body has an edge delimiting a top access opening, and wherein the first perimeter profile is a shoulder located internally to the rigid container body.

5. The mold according to claim 4, wherein the rigid cover has the lower surface, an upper or outer surface, and a perimeter edge for engagement with the edge of the rigid container body, and is configured so that the lower surface is insertable in the rigid container body, with the second perimeter profile in abutment against the shoulder.

6. The mold according to claim 5, wherein the second perimeter profile is provided on the lower surface of the rigid cover.

7. The mold according to claim 5, wherein, on the lower surface of the rigid cover, a perimeter recess is defined, so that the edge of the rigid container body is configured to be fit inserted, with interference, in the perimeter recess.

8. The mold according to claim 4, wherein the shoulder is provided inside the rigid container body at a substantially constant distance from the edge.

9. The mold according to claim 4, wherein the rigid container body has a plan configuration that is essentially shaped as a "C" and comprises a bottom wall substantially convex with a central portion and two end portions, the central portion being recessed with respect to the end portions.

10. The mold according to claim 9, wherein the rigid cover comprises at least one gripping portion between free ends of the "C".

11. The mold according to claim 4, wherein the rigid container body a perimetric stiffening rib, causing the rigid container body to be elastically undeformable.

12. The mold according to claim 1,
    wherein a plurality of openings are defined in the rigid cover so as to enable an overflow of bone cement poured into the rigid container body in excess, the plurality of openings further facilitating an overflow of air bubbles from the cavity.

13. The mold according to claim 12, wherein the plurality of opening are configured as flush openings in the rigid cover.

* * * * *